(12) United States Patent
Dupuis

(10) Patent No.: US 6,214,326 B1
(45) Date of Patent: Apr. 10, 2001

(54) COSMETIC COMPOSITION CONTAINING A CATIONIC POLYMER AND AN ACRYLIC TERPOLYMER, AND USE OF THIS COMPOSITION FOR THE TREATMENT OF KERATINOUS MATERIAL

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/332,004

(22) Filed: Jun. 14, 1999

(30) Foreign Application Priority Data

Jun. 15, 1998 (FR) .................................................. 98 07513

(51) Int. Cl.⁷ .............................. A61K 7/06; A61K 7/11; A61K 7/00
(52) U.S. Cl. ................. 424/70.1; 424/70.11; 424/70.12; 424/70.13; 424/70.15; 424/70.16; 424/70.17; 424/401
(58) Field of Search .................................... 424/401, 70.1, 424/70.11, 70.12, 70.13, 70.15, 70.16, 70.17

(56) References Cited

U.S. PATENT DOCUMENTS

| | | | |
|---|---|---|---|
| 4,445,521 | * | 5/1984 | Grollier et al. .......................... 132/7 |
| 4,514,552 | * | 4/1985 | Shay et al. ............................ 526/301 |
| 5,015,711 | | 5/1991 | Simonet et al. ....................... 526/301 |
| 5,066,710 | | 11/1991 | Simonet et al. ...................... 524/555 |
| 5,294,693 | | 3/1994 | Egraz et al. .......................... 526/310 |
| 5,362,415 | | 11/1994 | Egraz et al. ....................... 252/174.24 |
| 5,405,900 | * | 4/1995 | Jenkins et al. ........................ 524/556 |
| 5,561,189 | * | 10/1996 | Jenkins et al. ........................ 524/817 |
| 5,656,257 | * | 8/1997 | Fealy et al. ......................... 424/70.13 |
| 5,674,478 | * | 10/1997 | Dodd et al. ........................... 424/70.1 |
| 5,753,216 | * | 5/1998 | Leitch et al. ....................... 424/70.12 |
| 5,977,036 | * | 11/1999 | Guskey ................................ 510/121 |

FOREIGN PATENT DOCUMENTS

| | | |
|---|---|---|
| 0173109 | 3/1986 | (EP) . |
| 0350414 | 1/1990 | (EP) . |
| 0577526 | 1/1994 | (EP) . |
| 0 824 914 | 2/1998 | (EP) . |
| WO93/24544 | 12/1993 | (WO) . |

\* cited by examiner

Primary Examiner—Shelley A. Dodson
Assistant Examiner—Marina Lamm
(74) Attorney, Agent, or Firm—Jacobson, Price, Holman & Stern, PLLC

(57) ABSTRACT

Cosmetic composition containing a cationic polymer and an acrylic terpolymer, and use of this composition for the treatment of keratinous material. The present application relates to cosmetic compositions containing, in a cosmetically acceptable aqueous medium, at least one cationic polymer and an acrylic terpolymer, as well as to the use of these compositions for treating keratinous material.

The acrylic terpolymer comprises:
 a) about 20 to 70% by weight of a carboxylic acid containing α, β-monoethylenic unsaturation;
 b) about 20 to 80% by weight of a non-surfactant monomer containing monoethylenic unsaturation, which is different from a), and
 c) about 0.5 to 60% by weight of a nonionic urethane monomer which is the product of reaction of a monohydric nonionic surfactant with a monoisocyanate containing monoethylenic unsaturation.

The invention relates in particular to hair products containing, when they are in leave-in form, quaternized or non-quaternized vinylpyrrolidone/dialkylaminoalkyl acrylate or methacrylate copolymers or quaternized vinylpyrrolidone and vinylimidazole polymers.

26 Claims, No Drawings

COSMETIC COMPOSITION CONTAINING A CATIONIC POLYMER AND AN ACRYLIC TERPOLYMER, AND USE OF THIS COMPOSITION FOR THE TREATMENT OF KERATINOUS MATERIAL

The present invention relates to cosmetic compositions containing, in combination, at least one cationic polymer and an acrylic terpolymer, as well as to the use of these compositions for the treatment of keratinous material, in particular the hair.

Cationic polymers are used to give the hair good cosmetic properties such as softness, a pleasant feel and easy disentangling.

It is advantageous to formulate hair compositions containing cationic polymers, which have a high viscosity and are in a thickened liquid form which spreads well, such as a styling or care cream or gel, these properties being very much appreciated by consumers since the composition does not run down the forehead, the nape of the neck, the face or into the eyes.

For this, use is generally made of thickening and/or gelling polymers. However, the introduction of cationic polymers into thickeners often leads to problems of fluidization and of loss of clarity, and cosmetic performance levels obtained are sometimes insufficient for care products.

Thickening and/or gelling polymers are known which contain in their chain a hydrophilic part and a hydrophobic part consisting of a fatty chain, such as the product "Pemulen TR1" sold by the company Goodrich or the "Acrysol" polymers sold by the company Rohm & Haas. The polymer "Pemulen TR1", used in combination with cationic polymers, does not lead to a gel of satisfactory texture and does not give satisfactory cosmetic results, in particular as regards the fixing power, the softness and the feel. The polymer "Acrysol 44", used in combination with a cationic polymer, leads to a liquid and cloudy product.

The Applicant has discovered, surprisingly, that by using a novel family of thickening and/or gelling polymers and by combining them with cationic polymers, it is possible to obtain cosmetic formulations which have a satisfactory viscosity at a relatively low pH, which are not pasty or greasy, which spread well and which give the hair good properties of softness, feel and easy disentangling while at the same time having good fixing properties.

The subject of the present invention is thus cosmetic compositions containing, in a cosmetically acceptable aqueous support, at least one cationic polymer and an acrylic terpolymer which will be defined in greater detail later in the description.

This polymer makes it possible in particular to prepare gelled or thickened, leave-in or rinse-out, aqueous-organic or aqueous compositions containing cosmetically acceptable solvents.

The advantages of this terpolymer are that it is stable in electrolytic medium and has very good thickening power at a pH equal to or above 5.5, making it possible to achieve a good level of viscosity and to be able to use high concentrations of alcohol.

The acrylic terpolymer used in accordance with the invention is soluble or swellable in alkalis. It is characterized in that it comprises:

a) about 20 to 70% by weight, preferably 25 to 55% by weight, of a carboxylic acid containing α, β-monoethylenic unsaturation;

b) about 20 to 80% by weight, preferably 30 to 65% by weight, of a non-surfactant monomer containing monoethylenic unsaturation, which is different from a), and c) about 0.5 to 60% by weight, preferably 10 to 50% by weight, of a nonionic urethane monomer which is the product of reaction of a monohydric nonionic surfactant with a monoisocyanate containing monoethylenic unsaturation.

The carboxylic acid containing α, β-monoethylenic unsaturation a) can be chosen from many acids and in particular acrylic acid, methacrylic acid, itaconic acid and maleic acid. Methacrylic acid is preferred. A large proportion of acid is essential in order to give a polymer structure which dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation which has no surfactant properties. The preferred monomers are those which give polymers that are water-insoluble when they are homopolymerized and are illustrated by $C_1$–$C_4$ alkyl acrylates and methacrylates such as methyl acrylate, ethyl acrylate and butyl acrylate, or corresponding methacrylates. The monomers more particularly preferred are methyl and ethyl acrylates. Other monomers which can be used are styrene, vinyltoluene, vinyl acetate, acrylonitrile and vinylidene chloride. Non-reactive monomers are preferred, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobes generally consist of an aliphatic alcohol or an alkylphenol in which a carbon chain containing at least six carbon atoms constitutes the hydrophobic part of the surfactant.

The preferred monohydric nonionic surfactants have the formula:

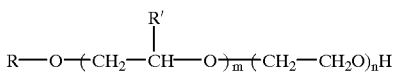

in which R is a $C_6$–$C_{30}$ alkyl or $C_8$–$C_{30}$ aralkyl group, R' is a $C_1$–$C_4$ alkyl group, n is an average number ranging approximately from 5 to 150 and m is an average number ranging approximately from 0 to 50, with the condition that n is at least as large as m and that n+m=5–150.

As preferred $C_6$–$C_{30}$ alkyl groups, mention may be made of dodecyl and $C_{18}$–$C_{26}$ alkyl radicals. As aralkyl groups, mention may be made more particularly of ($C_8$–$C_{13}$) alkylphenyl groups. The preferred group R' is the methyl group.

The monoisocyanate containing monoethylenic unsaturation which is used to form the nonionic urethane monomer c) can be chosen from a wide variety of compounds. A compound containing any copolymerizable unsaturation such as acrylic or methacrylic unsaturation can be used. An allylic unsaturation imparted by allyl alcohol can also be used. The preferred monoethylenic monoisocyanate is α,α-dimethyl-m-isopropenyl-benzylisocyanate.

The acrylic terpolymer defined above is obtained by aqueous emulsion copolymerization of the components a), b) and c) which is entirely common and described in patent application EP-A-0,173,109.

As terpolymers which can be used according to the invention, mention may be made of the products of reaction of methacrylic acid as component a), of ethyl acrylate as component b) and of a nonionic urethane macromonomer as component c), having the following structure:

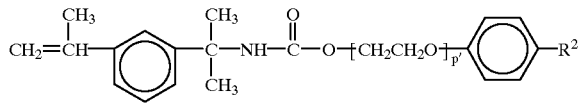

in which p' ranges from 6 to 150 and is preferably equal to 30 and $R^2$ is a $C_{8-C_{13}}$ alkyl radical, such as that described in Example 3 of patent application EP-A-0,173,109.

The preferred acrylic terpolymer used according to the invention is obtained from methacrylic acid as component a), methyl acrylate as component b) and a nonionic urethane macromonomer as component c), having the following structure:

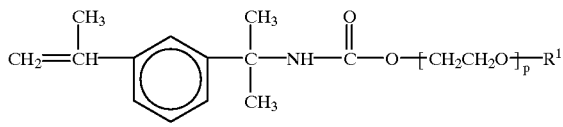

in which p ranges from 6 to 150 and $R^1$ is a $C_{18}$–$C_{26}$ alkyl radical, preferably $C_{20}$–$C_{24}$, linear, of plant origin, such as the docosyl radical.

The acrylic terpolymer is present in the cosmetic compositions of the invention in concentrations ranging from 0.01 to 20% by weight relative to the total weight of the composition, and preferably from 0.1 to 10% by weight.

The cationic polymers which can be used in accordance with the present invention can be chosen from any of those already known per se, in particular those described in patent application EP-A-0,337,354 and French patent applications FR-A-2,270,846, 2,383,660, 2,598,611, 2,470,596 and 2,519,863.

Even more generally, for the purposes of the present invention, the expression "cationic polymer" denotes any polymer containing cationic groups or groups which can be ionized into cationic groups.

The preferred cationic polymers are chosen from those which contain units containing primary, secondary, tertiary and/or quaternary amine groups which can either form part of the main polymer chain or which can be borne by a side substituent that is directly attached thereto.

The cationic polymers used generally have a molecular mass of between 500 and $5 \times 10^6$ approximately and preferably between $10^3$ and $3 \times 10^6$ approximately.

Among the cationic polymers, mention may be made more particularly of quaternized proteins (or protein hydrolysates) and polymers of the polyamine, polyaminoamide and quaternary polyammonium type. These are known products.

The quaternized proteins or protein hydrolysates are, in particular, chemically modified polypeptides bearing quaternary ammonium groups at the end of the chain or grafted thereto. Their molecular mass can range, for example, from 1500 to 10,000 and in particular from 2000 to 5000 approximately. Among these compounds, mention may be made in particular of:

collagen hydrolysates bearing triethyl-ammonium groups, such as the products sold under the name "Quat-Pro E" by the company Maybrook and referred to in the CTFA dictionary as "Triethonium Hydrolyzed Collagen Ethosulfate";

collagen hydrolysates bearing trimethyl-ammonium and trimethylstearylammonium chloride groups, sold under the name "Quat-Pro S" by the company Maybrook and referred to in the CTFA dictionary as "Steartrimonium Hydrolyzed Collagen";

protein hydrolysates bearing, on the polypeptide chain, quaternary ammonium groups containing at least one alkyl radical having from 1 to 18 carbon atoms.

Among these protein hydrolysates, mention may be made, inter alia, of:

"Croquat L" in which the quaternary ammonium groups contain a $C_{12}$ alkyl group;

"Croquat M" in which the quaternary ammonium groups contain $C_{10}$–$C_{18}$ alkyl groups;

"Croquat S" in which the quaternary ammonium groups contain a $C_{18}$ alkyl group;

"Crotein Q" in which the quaternary ammonium groups contain at least one alkyl group having 1 to 18 carbon atoms.

These various products are sold by the company Croda.

Other quaternized proteins or hydrolysates are, for example, those corresponding to the formula:

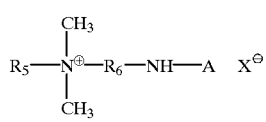

(I)

in which $X^\ominus$ is an anion of an organic or inorganic acid, A denotes a protein residue derived from collagen protein hydrolysates, $R_5$ denotes a lipophilic group containing up to 30 carbon atoms and $R_6$ represents an alkylene group having 1 to 6 carbon atoms. Mention may be made, for example, of the products sold by the company Inolex under the name "Lexein QX 3000", referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the name "Hydrotriticum WQ or QM", referred to in the CTFA dictionary as "Cocodimonium Hydrolysed Wheat Protein", "Hydrotriticum QL", referred to in the CTFA dictionary as "Lauridimonium Hydrolysed Wheat Protein" or alternatively "Hydrotriticum QS", referred to in the CTFA dictionary as "Steardimonium Hydrolysed Wheat Protein".

Another family of cationic polymers is that of cationic silicone polymers. Among these polymers, mention may be made of:

(a) silicone polymers corresponding to formula (II) below:

(II)

in which:

$G^1$, $G^2$, $G^3$ and $G^4$, which may be identical or different, denote a hydrogen atom, a phenyl group, an OH group, a $C_1$–$C_{18}$ alkyl group, for example methyl, a $C_2$–$C_{18}$ alkenyl group or a $C_1$–$C_{18}$ alkoxy group, a and a', which may be identical or different, denote the number 0 or an integer from 1 to 3, in particular 0, b denotes 0 or 1 and in particular 1, m and n are numbers such that the sum (n+m) can range especially from 1 to 2000 and in particular from 50 to 150, it being possible for n to denote a number from 0 to 1999 and in particular from 49 to 149 and it being possible for m to denote a number from 1 to 2000 and in particular from 1 to 10, $R_1$, $R_2$, $R_3$ and $R_4$, which may be identical or different, denote a monovalent radical of formula —$C_qH_{2q}O_sR^5L$ in which q is a number from 1 to 8, s and t, which may be identical or different, are equal to 0 or 1, $R^5$ denotes an optionally hydroxylated alkylene group and L is an optionally quaternized amine group chosen from the groups:

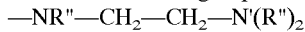
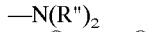
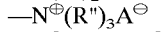
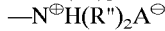
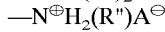
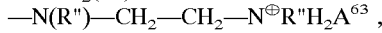

in which R" can denote hydrogen, phenyl, benzyl or a monovalent saturated hydrocarbon-based radical, for example an alkyl radical having from 1 to 20 carbon atoms and $A^\ominus$ represents a halide ion such as, for example, fluoride, chloride, bromide or iodide.

Products corresponding to this definition are, for example, the polysiloxanes referred to in the CTFA dictionary as "Amodimethicone" and corresponding to formula (II) below:

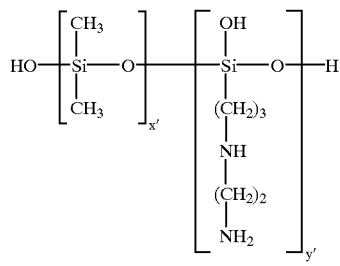

in which x' and y' are integers dependent on the molecular weight, generally such that the said molecular weight is between 5000 and 20,000 approximately.

A product corresponding to formula (II) is the polymer referred to in the CTFA dictionary as "Trimethylsilylamodimethicone", corresponding to the formula:

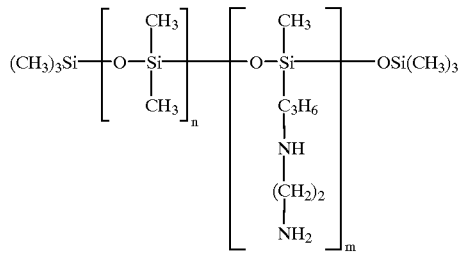

in which n and m have the meanings given above (cf. formula II).

A commercial product corresponding to this definition is a mixture (90/10 by weight) of a poly-dimethylsiloxane containing aminoethyl aminoisobutyl groups and of a polydimethylsiloxane, sold under the name "Q2-8220" by the company Dow Corning.

Such polymers are described, for example, in patent application EP-A-95238.

Other polymers corresponding to formula (II) are the silicone-based polymers corresponding to the following formula:

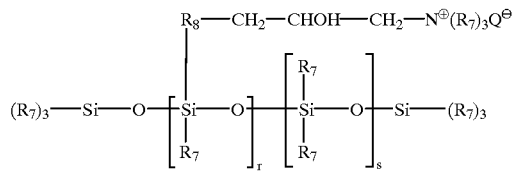

in which:

$R_7$ represents a monovalent hydrocarbon-based radical having from 1 to 18 carbon atoms, and in particular a $C_{1-C18}$ alkyl or $C_2$–$C_{18}$ alkenyl radical, for example methyl;

$R_8$ represents a divalent hydrocarbon-based radical, in articular a $C_{1-C18}$ alkylene radical or a $C_1$–$C_{18}$, for example $C_1$–$C_{8,}$ divalent alkylenoxy radical;

$Q^\ominus$ is a halide ion, in particular chloride;

r represents an average statistical value from 2 to 20 and in particular from 2 to 8;

s represents an average statistical value from 20 to 200 and in particular from 20 to 50.

Such polymers are described more particularly in US Pat. No. 4,185,087.

A polymer entering into this category is the polymer sold by the company Union Carbide under the name "Ucar Silicone ALE 563".

When these silicone-based polymers are used, one particularly advantageous embodiment is to use them together with cationic and/or nonionic surfactants. It is possible to use, for example, the product sold under the name "Cationic Emulsion DC 929" by the company Dow Corning, which comprises, besides amodimethicone, a cationic surfactant comprising a mixture of products corresponding to the formula:

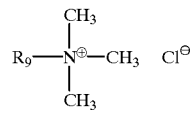

in which $R_9$ denotes alkenyl and/or alkyl radicals having from 14 to 22 carbon atoms, derived from tallow fatty acids, in combination with a nonionic surfactant of formula:

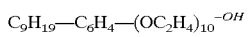

known under the name "Nonoxynol 10".

Another commercial product which can be used according to the invention is the product sold under the name "Dow Corning Q2 7224" by the company Dow Corning, containing, in combination, trimethylsilyl-amodimethicone of formula (IV), a nonionic surfactant of formula:

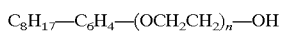

in which n=40, also known as "Octoxynol-40", another nonionic surfactant of formula:

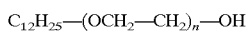

in which n=6, also known as "Isolaureth-6", and glycol.

The polymers of the polyamine, polyaminoamide or polyquaternary ammonium type which can be used in accordance with the present invention and which can be mentioned in particular are those described in French patents Nos. 2,505,348 and 2,542,997. Among these polymers, mention may be made of:

(1) Quaternized or non-quaternized vinyl-pyrrolidone/dialkylaminoalkyl acrylate or methacrylate copolymers, such as the products sold under the name "Gafquat" by the company ISP, such as, for example, "Gafquat 734, Gafquat 755 or Gafquat HS100" or alternatively the products known as "Copolymer 937" or "Copolymer 845". These polymers are described in detail in French patents 2,077,143 and 2,393,573.

(2) The cellulose ether derivatives containing quaternary ammonium groups described in French patent 1,492,597, and in particular the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

The commercial products corresponding to this definition are, more particularly, the products sold under the names "Celquat L 200" and "Celquat H 100" by the company National Starch.

(4) Cationic polysaccharides, and in particular guar gums, described more particularly in U.S. Pat. Nos. 3,589,578 and 4,031,307 and more particularly the products sold under the names "Jaguar C 13 S", "Jaguar C 15" and "Jaguar C 17" sold by the company Meyhall.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2,162,025 and 2,280,361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide; these polyaminoamides can be alkylated or, if they contain one or more tertiary amine functions, they can be quaternized. Such polymers are described in particular in French patents 2,252,840 and 2,368,508.

(7) Polyaminoamide derivatives resulting from the condensation of polyalkylenepolyamines with polycarboxylic acids followed by an alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363.

Among these derivatives, mention may be made more particularly of the adipic acid/dimethylamino-hydroxypropyl/diethylenetriamine polymers sold under the name "Cartaretine F", "Cartaretine F4" or "Cartaretine F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms, the molar ratio between the polyalkylenepolyamine and the dicarboxylic acid being between 0.8:1 and 1.4:1, the polyaminoamide resulting therefrom being reacted with the epichlorohydrin in a molar ratio of epichlorohydrin relative to the secondary amine group in the polyaminoamide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or under the name "PD 170" or "Delsette 101" by the company Hercules in the case of the adipic acid/epoxypropyl/diethylenetriamine copolymer.

(9) Methyldiallylamine or dimethyldiallyl-ammonium cyclopolymers such as polymers containing, as constituents of the chain, units corresponding to formula (VI) or (VI'):

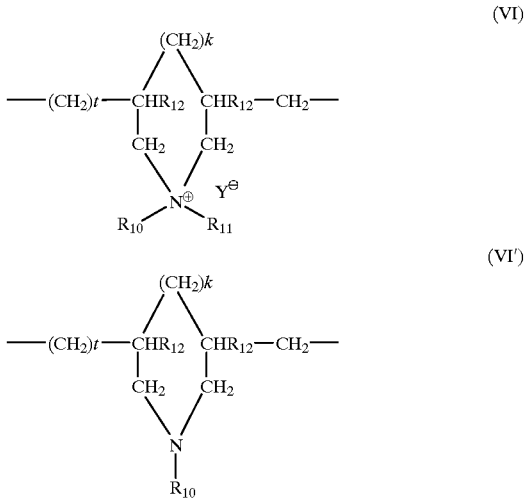

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, a lower amidoalkyl group or $R_{10}$ and $R_{11}$ can denote, together with the nitrogen atom to which they are attached, heterocyclic groups such as piperidyl or morpholinyl; $Y^{\ominus}$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallyl-ammonium chloride homopolymer sold under the name "Merguat 100" by the company Merck, and the copolymers of dimethyl-diallylammonium chloride and of acrylamide sold under the name "Merquat 550".

(10) The quaternary diammonium polymer containing repeating units corresponding to the formula:

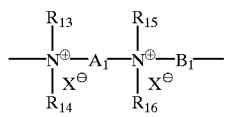

(VII)

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl, amide or —CO—O—$R_{17}$—D or —CO—NH—$R_{17}$—D group in which $R_{17}$ is an alkylene and D is a quaternary ammonium group;

$A_1$ and $B_1$ represent polymethylene groups containing from 2 to 20 carbon atoms which can be linear or branched, saturated or unsaturated, and which can contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^{\ominus}$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$ in which D denotes:

a) a glycol residue of formula: —O—Z—O, in which Z denotes a linear or branched hydrocarbon radical or a group corresponding to one of the following formulae:

—(CH$_2$—CH$_2$—O)$_x$—CH$_2$

—[CH$_2$—CH(CH$_3$)—O]$_y$—CH$_2$—CH(CH$_3$)— in which x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH, in which Y denotes a linear or branched hydrocarbon-based radical or alternatively the divalent radical

—CH$_2$—CH$_2$—S—S—CH$_2$—CH$_2$—;

d) a ureylene group of formula:

NH—CO—NH—.

Preferably, $X^{\ominus}$ is an anion such as chloride or bromide.

These polymers have a molecular mass generally of between 1000 and 100,000.

Polymers of this type are described in articular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Polyquaternary ammonium polymers consisting of units of formula (VIII):

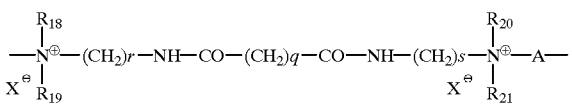

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$ OH radical, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X denotes a halogen atom, A denotes a radical of a dihalide or preferably represents —CH$_2$—CH$_2$—O—CH$_2$—CH$_2$—.

Such compounds are described in particular in patent application EP-A-122,324.

Among those, mention may be made, for example, of the products "Mirapol A 15", "Mirapol 10 AD1", "Mirapol AZ1" and "Mirapol 175" sold by the company Miranol.

(12) Homopolymers or copolymers derived from acrylic or methacrylic acid and containing units:

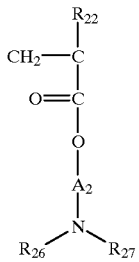

-continued

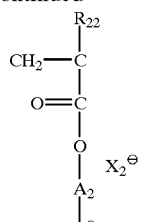

and/or

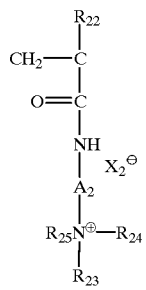

in which the groups $R_{22}$ independently denote H or $CH_3$, the groups $A_2$ independently denote a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl radical, the groups $R_{26}$ and $R_{27}$ represent a hydrogen atom or an alkyl group of 1 to 6 carbon atoms, $X_2^{\ominus}$ denotes an anion, for example methosulphate or halide, such as chloride or bromide.

The comonomer(s) which can be used in the preparation of the corresponding copolymers belong(s) to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary vinylpyrrolidone and vinyl-imidazole polymers such as, for example, the products sold under the names "Luviquat FC 905", "Luviquat FC 550" and "Luviquat FC 370" by the company BASF.

(14) Polyamines such as "Polyquart H" sold by Henkel referred to under the name "Polyethylene glycol (15) Tallow Polyamine" in the CTFA dictionary.

(15) Methacryloyloxyethyltrimethylammonium chloride crosslinked polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. An acrylamide/ methacryloyloxyethyltrimethylammonium chloride crosslinked copolymer (20/80 by weight) in the form of a dispersion containing 50% by weight of the said copolymer in mineral oil can be used more particularly. This dispersion is sold under the name "Salcare SC 92" by the company Allied Colloids. A methacryloyloxyethyltrimethyl-ammonium chloride crosslinked homopolymer containing about 50% by weight of the homopolymer in mineral oil can also be used. This dispersion is sold under the name "Salcare SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all of the cationic polymers which can be used in the context of the present invention, it is preferred to use, in the leave-in products, quaternized or non-quaternized vinylpyrrolidone/dialkylaminoalkyl acrylate or methacrylate copolymers, such as the products sold under the name "Gafquat" by the company ISP, such as, for example, "Gafquat 734, Gafquat 755 or Gafquat HS 100" or alternatively the products known as "Copolymer 937" or "Copolymer 845" also sold by the company ISP, and quaternary vinylpyrrolidone and vinylimidazole polymers such as the products sold under the names "Luviquat FC 905", "Luviquat FC 550" and "Luviquat FC 370" by the company BASF.

According to the invention, cationic polymers in latex or pseudolatex form, i.e. in the form of a dispersion of insoluble polymer particles, can also be used.

The cationic polymers are used in the compositions of the invention in proportions of between 0.01 and 20% by weight and preferably between 0.1 and 8% by weight relative to the total weight of the composition.

The compositions according to the invention contain a cosmetically acceptable aqueous medium. They have a pH which can range from 3.5 to 11, preferably between 5.5 and 11 and- even more preferably between 5.5 and 8.5.

The cosmetically acceptable medium for the compositions according to the invention consists more particularly of water and optionally of cosmetically acceptable organic solvents.

The organic solvents can represent from 0.5 to 90% of the total weight of the composition. They can be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, polyethylene glycols having from 6 to 80 ethylene oxide units, and polyols.

As amphiphilic organic solvents, mention may be made of polypropylene glycol (PPG) derivatives, such as esters of polypropylene glycol and of fatty acid, derivatives of PPG and of fatty alcohol, such as PPG-23 oleyl ether, and PPG-36 oleate.

As lipophilic organic solvents, mention may be made, for example, of fatty esters such as diisopropyl adipate, dioctyl adipate, alkyl benzoates and dioctyl malate.

In order for the cosmetic compositions of the invention to be more pleasant to use (softer when applied, more nourishing and more emollient), it is possible to add a fatty phase to the medium of these compositions.

The fatty phase can represent up to 50% of the total weight of the composition.

This fatty phase can contain an oil or a wax or mixtures thereof, and can also comprise fatty acids, fatty alcohols and fatty acid esters. The oils can be chosen from animal, plant, mineral or synthetic oils and in particular from liquid petroleum jelly, liquid paraffin, isoparaffins, poly-α-olefins, fluoro oils and perfluoro oils. Similarly, the waxes can be chosen from animal, fossil, plant, mineral or synthetic waxes which are known per se.

The compositions of the invention can contain adjuvants that are common in the cosmetics field, such as other standard gelling agents and/or thickeners; emulsifiers; surfactants; moisturizers; emollients; hydrophilic or lipophilic active agents such as ceramides; anti-free-radical agents; sequestering agents; antioxidants; preserving agents; acidifying or basifying agents; fragrances; fillers; dyestuffs; modified or non-modified, volatile or non-volatile silicones; reducing agents. The amounts of these various adjuvants are those used conventionally in the fields considered.

Needless to say, a specialist will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in any form which is suitable for topical application, in particular in the form of a thickened lotion, in the form of aqueous or aqueous-alcoholic gels, in the form of vesicle dispersions or in the form of simple or complex emulsions (O/W, W/O, O/W/O or W/O/W emulsions) and can be of liquid, semi-liquid or solid consistency, such as creams, milks, gels, cream-gels, pastes and sticks, and can optionally be packaged as an aerosol and can be in the form of mousses or sprays. These compositions are prepared according to the usual methods.

The compositions according to the invention are preferably used as rinse-out or leave-in hair products, in particular to wash, dye, care for, condition or straighten the hair, to maintain the hairstyle or to permanently or temporarily reshape the hair.

The compositions can be styling products such as hair-setting lotions, blow-drying lotions, fixing compositions and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray or a mousse for fixing or treating the hair.

The compositions of the invention can also be shampoos, rinse-out compositions or leave-in compositions, to be applied before or after shampooing, dyeing, bleaching, permanent-waving or straightening the hair.

The compositions of the invention can also be used as hygiene or care products, such as protective, treatment or care creams for the face, for the hands or for the body, protective or care body milks, and skincare or skin cleansing lotions, gels or mousses.

The compositions can also consist of solid preparations constituting cleansing soaps or bars.

The compositions of the invention can also be used as oral care products such as toothpastes and mouthwashes.

The compositions can be make-up products such as face creams, foundations, mascaras, eyeliners, lipsticks or nail varnishes.

Another subject of the invention is a cosmetic, non-therapeutic treatment process for the skin, the scalp, the hair, the eyelashes, the eyebrows, the nails or the mucous membranes, characterized in that a composition as defined above is applied to the keratinous support, according to the usual technique for using this composition, for example application of creams, gels, sera, lotions or milks to the skin, the scalp or the mucous membranes.

According to the invention, the hair is treated more particularly.

The examples which follow illustrate the invention without being limiting in nature.

EXAMPLE 1
Leave-In Haircare Gel

Ethoxylated (40 EO) methacrylic acid/methyl acrylate/behenyl dimethylmetaisopropenyl-benzylisocyanate terpolymer as an aqueous 25% dispersion 0.5 g AM Vinylpyrrolidone/methylvinylimidazolium chloride copolymer (70/30) as an aqueous 40% solution, sold by the company BASF under the trade name "Luviquat FC 370" 0.5 g AM 2-Amino-2-methyl-l-propanol (AMP), qs pH adjusted to 7.5

Fragrance, preserving agent, dye qs

Demineralized water qs 100 g

A fluid, non-pasty, non-greasy gel which spreads very well on the hair is obtained. This gel makes the hair feel soft, makes it easy to disentangle and has good fixing power.

If the above terpolymer is replaced by the same amount of "Acrysol 44" polyurethane from Rohm & Haas, a cloudy, liquid product is obtained.

If the terpolymer is replaced by the crosslinked acrylic acid/$C_{10}/C_{30}$ alkyl acrylate copolymer "Pemulen TR1" sold by Goodrich, a slightly pasty gel with very mediocre fixing power and considerably inferior cosmetic properties of softness and feel is obtained.

EXAMPLE 2
Shampoo

Sodium lauryl ether sulphate containing 2.2 mol of ethylene oxide 15 g AM

Cocoylbetaine 2.5 g AM

Ethoxylated (40 EO) methacrylic acid/methyl acrylate/behenyl dimethylmetaisopropenyl-benzylisocyanate terpolymer as an aqueous 25% dispersion 1 g AM Hydroxypropylguar triethylammonium chloride, sold under the name "Jaguar C13S" by the company Meyhall 0.1 g Preserving agents, fragrance qs Water qs 100 g pH adjusted to 6.5 (NaOH)

This shampoo has the appearance of a thickened liquid. It has good foaming properties and leaves the hair smooth and easy to disentangle after shampooing.

COMPARATIVE EXAMPLE 3
Shampoo

Sodium lauryl ether sulphate containing 2.2 mol of ethylene oxide 15 g AM

Cocoylbetaine 2.5 g AM

Polyethoxylated polyurethane with an alkyl end, as a 35% solution in a propylene glycol/water mixture (60/40) ("Acrysol 44" sold by the company Rohm & Haas) 1 g AM Hydroxypropylguar triethylammonium chloride, sold under the name "Jaguar C13S" by the company Meyhall 0.1 g Preserving agents, fragrance qs Water qs 100 g pH adjusted to 6.5 (NaOH)

This shampoo has the appearance of a very fluid, cloudy product and has cosmetic properties that are very much inferior to those of the shampoo according to the invention: the dried hair is less smooth and is more difficult to disentangle.

EXAMPLE 4
Leave-In Styling Gel

Vinylpyrrolidone/dimethylaminoethyl methacrylate copolymer quaternized with diethyl sulphate, at 50% in ethanol, sold under the name "Guafquat 734" by the company ISP 1 g AM Ethoxylated (40 EO) methacrylic acid/methyl acrylate/behenyl dimethylmetaisopropenyl-benzylisocyanate terpolymer as an aqueous 25% dispersion 1 g AM Absolute ethanol 8.7 g Fragrance, preserving agent, dye qs 2-Amino-2-methyl-1-propanol (AMP), qs pH adjusted to 7.5

Demineralized water qs 100 g

A fluid, non-pasty, non-greasy gel which spreads well on the hair is obtained. This gel makes the hair feel soft, makes it easy to disentangle and has good fixing power.

What is claimed is:

1. Cosmetic composition for the treatment of keratinous material comprising in a cosmetically acceptable aqueous medium, at least one cationic polymer and an acrylic terpolymer comprising:

a) about 20 to 70% by weight, of a carboxylic acid containing α, β-monoethylenic unsaturation;

b) about 20 to 80% by weight, of a non-surfactant monomer containing monoethylenic unsaturation, which is different from a); and c) about 0.5 to 60% by weight, and preferably 10 to 50% by weight, of a nonionic urethane monomer which is the product of reaction of a monohydric nonionic surfactant with a monoisocyanate containing monoethylenic unsaturation.

2. Composition according to claim 1, wherein the carboxylic acid containing α,βmonoethylenic unsaturation a) is acrylic acid, methacrylic acid, itaconic acid or maleic acid.

3. Composition according to claim 2, wherein the carboxylic acid containing α,βmonoethylenic unsaturation a) is methacrylic acid.

4. Composition according to claim 3 wherein the non-surfactant monomer containing monoethylenic unsaturation b) is $C_{1-C4}$ alkyl acrylates or methacrylates, styrene, vinyltoluene, vinyl acetate, acrylonitrile or vinylidene chloride.

5. Composition according to claim 4, wherein the non-surfactant monomer containing monoethylenic unsaturation is methyl or ethyl acrylate.

6. Composition according to any one of claim 1 wherein the monohydric nonionic surfactant used to obtain the nonionic urethane monomer c) has the formula:

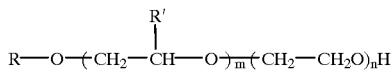

in which R is a $C_6$–$C_{30}$ alkyl or $C_8$–$C_{30}$ aralkyl group, R' is a $C_1$–$C_4$ alkyl group, n is an average number ranging from about 5 to 150 and m is an average number ranging from about 0 to 50, with the condition that n is at least as large as m and that n+m=5–150.

7. Composition according to claim 6 wherein R is a dodecyl, $C_{18}$–$C_{26}$ alkyl or ($C_{8-C13}$) alkylphenyl group, m=0 and n is an average number ranging from about 5 to 150.

8. Composition according to claims 1 wherein the monoisocyanate containing monoethylenic unsaturation which is used to form the nonionic urethane monomer c) is α,α-dimethyl-m-isopropenyl benzyl isocyanate.

9. Composition according to claim 1 wherein the acrylic terpolymer is an aqueous dispersion obtained from methacrylic acid as component a) methyl acrylate as component b) and a nonionic urethane macromonomer of the following structure:

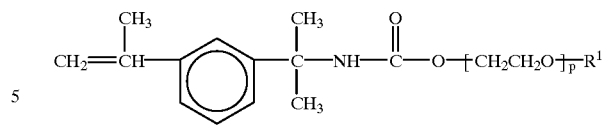

in which p ranges from 6 to 150 and R' is a $C_{18}$–$C_{26}$ alkyl radical.

10. Composition according to claim 1 wherein the acrylic terpolymer is present in concentrations ranging from 0.01 to 20% by weight, relative to the total weight of the composition.

11. Composition according to claim 1 wherein the cationic polymers are quaternized proteins or protein hydrolysates, silicone-based cationic polymers, quaternized or non-quaternized vinylpyrrolidone/dialkylaminoalkyl acrylate or methacrylate copolymers, cellulose ether derivatives containing quaternary ammonium groups, cationic cellulose derivatives, cationic polysaccharides, polymers consisting of piperazinyl units and of divalent alkylene or hydroxyalkylene radicals, water-soluble polyaminoamides prepared by polycondensation of an acidic compound with a polyamine, polyaminoamide derivatives resulting from the condensation of polyalkylenepolyamines with polycarboxylic acids followed by an alkylation with difunctional agents, polymers obtained by reaction of a polyalkylenepolyamine containing two primary amine groups and at least one secondary amine group with a dicarboxylic acid, methyldiallylamine or dimethyl-diallylammonium cyclopolymers, quaternary diammonium polymers, polyquaternary ammonium polymers, homopolymers or copolymers derived from acrylic or methacrylic acid, containing ester or amide units substituted with a group containing an amine or quaternary ammonium function, quaternary vinylpyrrolidone or vinylimidazole polymers, polyamines, methacryloyloxyethyltrimethylammonium chloride crosslinked polymers and mixtures thereof.

12. Composition according to claim 11, wherein the composition is of leave-in type and comprises one or more quaternized or non-quaternized vinylpyrrolidone/dialkylaminoalkyl acrylate or methacrylate copolymers or quaternary vinylpyrrolidone or vinylimidazole polymers.

13. Composition according to claim 1 wherein the cationic polymer(s) are present in concentrations ranging from 0.01 to 20% by weight, relative to the total weight of the composition.

14. Composition according to claim 1 wherein the composition has a pH ranging from 3.5 to 11.

15. Composition according to claim 1 wherein the cosmetically acceptable aqueous medium consists of water or of water and at least one organic solvent selected from the group consisting of hydrophilic, lipophilic and amphiphilic organic solvents and mixtures thereof.

16. Composition according to claim 1, further comprising at least one fatty substance, gelling agent and/or thickener, surfactant, moisturizer, emollient, hydrophilic or lipophilic active agent, anti-free-radical agent, sequestering agent, antioxidant, preserving agent, acidifying or basifying agent, fragrance, filler, dyestuff, silicone or reducing agent.

17. Composition according to claim 1 wherein the composition is in the form of an emulsion, a lotion, a gel, a vesicle dispersion, a paste or a solid stick or is packaged as an aerosol and is in the form of a mousse or a spray.

18. Composition according to claim 1 wherein the composition is used as a rinse-out or leave-in hair product to wash, dye, care for, condition or straighten the hair, to maintain the hairstyle or to permanently or temporarily reshape the hair.

19. Cosmetic, non-therapeutic treatment process for treating keratinous material comprising applying an effective amount of a composition as defined in claim 1 to the keratinous material.

20. Composition according to claim 1, wherein the acrylic terpolymer comprises about 25 to 55% by weight of the carboxylic acid containing α,β-monoethylenic unsaturation, about 30 to 65% by weight of the non-surfactant monomer containing monoethylenic unsaturation and about 10 to 50% by weight of the nonionic urethane monomer.

21. Composition according to claim 9, wherein $R^1$ is a linear $C_{20}$–$C_{24}$ alkyl radical of plant origin.

22. Composition according to claim 21, wherein the alkyl radical of plant origin is the docosyl radical.

23. Composition according to claim 10, wherein the concentration of acrylic terpolymer is from 0.1 to 10% by weight.

24. Composition according to claim 13, wherein the cationic polymers are present in concentrations ranging from 0.1 to 8% by weight.

25. Composition according to claim 14, wherein the pH range is from 5.5 to 8.5.

26. Cosmetic, non-therapeutic treatment process according to claim 19, wherein the keratinous material is hair.

* * * * *